US012642704B2

(12) United States Patent
Vadelund et al.

(10) Patent No.: US 12,642,704 B2
(45) Date of Patent: Jun. 2, 2026

(54) FLEXIBLE HEMOSTATIC PAD

(71) Applicant: BioLife Delaware, L.L.C., South Jordan, UT (US)

(72) Inventors: Kurt Vadelund, Apollo Beach, FL (US); Talmadge Kelly Keene, Ruskin, FL (US); Kenneth Wiglund, Bradenton, FL (US); Mark Travi, Venice, FL (US)

(73) Assignee: Biolife Delaware, L.L.C., South Jordan, UT (US)

( * ) Notice: Subject to any disclaimer, the term of this patent is extended or adjusted under 35 U.S.C. 154(b) by 0 days.

(21) Appl. No.: 17/168,117

(22) Filed: Feb. 4, 2021

(65) Prior Publication Data

US 2022/0192891 A1 Jun. 23, 2022

Related U.S. Application Data

(60) Provisional application No. 62/969,716, filed on Feb. 4, 2020.

(51) Int. Cl.
| | |
|---|---|
| *A61F 13/02* | (2024.01) |
| *A61F 13/00* | (2024.01) |
| *A61F 13/01* | (2024.01) |
| *A61L 15/42* | (2006.01) |
| *A61L 15/44* | (2006.01) |

(52) U.S. Cl.
CPC .... *A61F 13/0233* (2013.01); *A61F 13/00063* (2013.01); *A61F 13/01021* (2024.01); *A61F 13/0289* (2013.01); *A61L 15/42* (2013.01); *A61L 15/44* (2013.01); *A61F 2013/00238* (2013.01); *A61L 2300/102* (2013.01);
(Continued)

(58) Field of Classification Search
CPC ........... A61F 13/0233; A61F 13/00063; A61F 13/0289; A61F 13/023; A61F 13/00021; A61F 2013/00238; A61L 15/42; A61L 15/44; A61L 2300/418; A61L 2300/60; A61L 2400/04
See application file for complete search history.

(56) References Cited

U.S. PATENT DOCUMENTS

| | | | |
|---|---|---|---|
| 6,187,347 B1 | 2/2001 | Patterson et al. | |
| 6,521,265 B1 * | 2/2003 | Patterson ............. | A61K 47/585 424/407 |

(Continued)

FOREIGN PATENT DOCUMENTS

| | | | | |
|---|---|---|---|---|
| ES | 2358098 T3 * | 5/2011 | ............. | A61K 31/14 |
| JP | 2003-531850 A | 10/2003 | | |

(Continued)

OTHER PUBLICATIONS

International Search Report and Written Opinion for PCT/US2021/016686, May 19, 2021, 15 pages.
(Continued)

*Primary Examiner* — Rachael E Bredefeld
*Assistant Examiner* — Seth R. Brown
(74) *Attorney, Agent, or Firm* — Dorsey & Whitney LLP

(57) ABSTRACT

A flexible hemostatic pad formed from a hemostatic powder, which may contain a hydrophilic polymer such as a cation ion exchange resin, compressed onto or into a velvet-like backing substrate is provided for the control of bleeding at a wound site.

14 Claims, 12 Drawing Sheets

(52) U.S. Cl.
CPC ..... *A61L 2300/418* (2013.01); *A61L 2300/60* (2013.01); *A61L 2400/04* (2013.01)

(56) References Cited

U.S. PATENT DOCUMENTS

| | | | | |
|---|---|---|---|---|
| 8,821,848 B1 * | 9/2014 | Keene | ................... | A61K 31/79 424/78.06 |
| 8,961,479 B2 | 2/2015 | Hen et al. | | |
| 2002/0141964 A1 * | 10/2002 | Patterson | ............... | A61K 31/14 424/661 |
| 2006/0155235 A1 * | 7/2006 | Sawyer | ............... | A61F 13/0203 602/48 |
| 2008/0095830 A1 * | 4/2008 | Van Holten | ............. | A61L 15/32 424/94.64 |
| 2009/0252799 A1 * | 10/2009 | Hen | ...................... | A61L 26/008 424/647 |
| 2010/0129427 A1 * | 5/2010 | Hen | ........................ | A61L 15/28 424/445 |
| 2010/0226873 A1 * | 9/2010 | Hen | ........................ | A61P 17/02 424/78.06 |
| 2014/0120052 A1 | 5/2014 | Hen et al. | | |
| 2014/0330221 A1 * | 11/2014 | Hen | ........................ | A61L 15/18 424/464 |
| 2017/0232141 A1 * | 8/2017 | Surti | ................... | A61F 13/0253 602/61 |
| 2018/0008474 A1 * | 1/2018 | Jan | ........................ | A61L 15/425 |

FOREIGN PATENT DOCUMENTS

| | | | |
|---|---|---|---|
| JP | 2016-523107 | A | 8/2016 |
| WO | WO2001082896 | A1 | 11/2001 |
| WO | 2008051758 | | 5/2008 |
| WO | 2009130485 | | 10/2009 |
| WO | 2013113906 | | 8/2013 |
| WO | WO2014153566 | A2 | 9/2014 |

OTHER PUBLICATIONS

Office Action for Japanese Application No. 2022-547776, Dec. 4, 2024, 4 pages.

* cited by examiner

FLEXIBLE HEMOSTATIC PAD

FIELD OF THE INVENTION

The present invention relates generally to a topically applied, flexible hemostatic pad to control and/or arrest bleeding and methods of making such pads.

BACKGROUND OF THE INVENTION

Hemostatic products are known in the prior art, in both powder and tablet form. For example, hemostatic products composed of greater than 80% hydrogen resin have been used in both powder and rigid tablet forms to diminish and/or stop bleeding and absorb exudate. The powder forms typically conform to any wound surface regardless of shape, including curved surfaces like a finger, but may be messy to use. In addition, some powder forms may not adhere sufficiently to the wound site. Tablet forms are typically rigid and may break or crack when subjected to a force. To overcome this propensity of breaking, tablet forms must be made relatively thick as compared to the diameter. In addition, due to the inflexibility, rigid compressed powder tablets can only be used on relatively flat or small-dimension surfaces. Hemostatic compressed powder tablets, for example, have heretofore been known as useful for vascular access procedures where bleeding control is necessary at the arterial puncture site and where the site is relatively flat or small in surface area. However, when the wound area is at or on a body part that is round (such as a finger, arm, or leg), uneven, or larger in surface area, the tablet products are not as useful due to their lack of mechanical flexibility.

Hemostatic tablets may also suffer from a weakened structural strength which may manifest as cracking during transport and assembly. The product must arrive to the customer intact and, thus, sufficiently strong. Tablets have a limit in size due to the thickness to surface area ratio to make a structurally sound tablet. In order to prevent cracking and provide for sufficient structural strength, tablets may be overly thick and, thus, cosmetically unacceptable. Larger tablets are also more susceptible to improper application on a curved wound surface. For example, a small tablet can be applied to a location on a wrist or finger to stop bleeding on a small wound, but a large tablet could not wrap around a wrist or finger for a larger wound that is along the curved surface of the wrist. The same could be said of nearly any tablet on a finger.

One example of a powder hemostatic product is disclosed in Patterson et al., U.S. Pat. No. 6,187,347 ("Patterson"), which is incorporated herein in its entirety by reference thereto, discloses a free flowing powder to arrest bleeding from a wound by (1) providing a substantially anhydrous compound of a salt ferrate which will hydrate in the presence of blood to produce $Fe^{+++}$ to clot blood and produce oxygen; and (2) applying this compound to the wound for a time sufficient for arresting blood flow, reducing the microbial population, and forming a protective coating over the wound. In one embodiment, an acid cation exchange material (in the form of a hydrogen resin) is mixed with salt ferrate to provide a protective coating over the wound for protection. The combination of salt ferrate and an acid cation exchange resin produces $Fe^{+++}$ in a form that allows the iron cation to covalently interact with blood to effect coagulation and create a protective scab over the wound with antimicrobial properties.

In making the wound sealing powder disclosed by Patterson, the cation exchange resin is prepared in the washed hydrogen form, dried at approximately 110° C. for 24 hours and then powdered in a grinder to about 100 mesh size. A 100-mesh powder particle is 149 microns (or 0.149 mm) in diameter.

WoundSeal® topical powder, also commercially available from Biolife LLC, currently consists of a hydrophilic polymer (such as the hydrogen resin referred to above) and potassium ferrate. To use WoundSeal® topical powder, the wound is first cleaned, and the powder is poured onto the wound after bleeding resumes because blood must be present for the powder to work. The powder is then compressed over the wound to stop bleeding, which results in a messy application due to the powder.

WoundSeal® topical powder is typically made from an approximately weight mixture of potassium ferrate and a hydrophilic polymer (hydrogen resin). Weight mixtures ranging from 1:3 to 1:12 will typically arrest bleeding, depending on the particular application. In one embodiment, the ferrate (after grinding) and the resin (after drying) are mixed and then ground in a Turbo Mill, which is a rotor mill style grinder that utilizes a high speed rotor contained in a grinding chamber with a screen that reduces the particle size through impact with the rotor and screen. The particle size is controlled via rotor speed and screen opening size. Based on the size of the unground beads and the size of the openings in the grinding screen, a fraction of the unground (whole) bead will pass through the grinding process and there is typically no post-grind screening process.

The Turbo Mill has a continuous feed into the mill, and a continuous flow of particles out of the mill of particles that have passed through the control screen. The screen used in this embodiment is a 1 mm screen and the mill is run at a production speed sufficient to obtain the WoundSeal® topical powder. After production, the powder is stored in closed containers, such as plastic tubs, in order to deter re-hydration until the powder can be packaged in consumer-ready packaging for sale.

As noted above, hemostatic products other than powders are also known in the art. For example, U.S. Pat. No. 8,961,479, Hen, et al., ("Hen") which is incorporated herein in its entirety by reference thereto, discloses a tablet form of a compressed hemostatic agent made from a hemostatic powder that may include potassium ferrate and a hydrophilic polymer (cation ion exchange resin—sometimes referred to as a hydrogen resin). The powder is pressure formed into a rigid tablet for delivery to a bleeding wound. The tablet improves the rate of adhesion to a bleeding wound surface, and allows a significantly greater and more uniform pressure to be exerted by manual compression of the tablet on the wound site, as compared to that of a thin layer of scattered hemostatic powder. Sometime after the seal is formed from the interaction of blood or exudates with the immediate contacting surface of the tablet, the bulk of the unused tablet delaminates, due to expansion from moisture absorption at the blood tablet interface, from the seal making clean-up easier. If the unused portion of the tablet is not removed from the wound site, a reservoir of hemostatic dressing stops further bleeding. The tablet may be applied to any surface orientation and take any shape and thickness possible. Unlike known hemostatic powders, a tablet may be applied to a vertical surface.

The compressed hemostatic tablet of Hen is a rigid, non-flexible product that will crack and break if sufficiently bent. The commercial form of the hemostatic tablet is sold by Biolife, LLC of Sarasota, Florida, under the trademark StatSeal® Disc. While useful in many situations for arresting the flow of blood, and in particular when used in various vascular procedures, the Hen hemostatic tablet is not as useful on body parts that are not flat or that are not relatively small in surface area. The maximum surface area of a StatSeal® Disc can be calculated from a 22 mm diameter round tablet. To allow the StatSeal® Disc to fit around an indwelling vascular catheter, the tablet is made in two parts and employs a foam assemblage to allow it to flex open and then close around the catheter line.

Currently, the StatSeal® Disc is made with hydrophilic polymer (hydrogen form of ion exchange resin) and potassium ferrate. The hydrogen resin before combining with the ferrate and compressing is dried so that the resin does not react with the ferrate.

The foregoing examples of the related art and limitations related thereto are intended to be illustrative and not exclusive. Other limitations of the related art will become apparent to those skilled in the art upon a reading of the specification and a study of the drawings.

SUMMARY OF INVENTION

Briefly, the present invention is directed, in an embodiment, to a hemostatic product comprising a compressed hemostatic powder pad that is flexible and can bend in order to be applied to a curved surface without breaking. The present invention relates generally to topically applied flexible hemostatic pads that arrest bleeding. The pad is created by compression of a hemostatic powder incorporated into a fibrous velvet-like backing. The resulting pad is flexible and may be conveniently applied to any wound surface, regardless of shape, compared to an inflexible tablet that is made without the velvet-like material. The resulting pad may be cut into shapes during manufacturing, and the size or length of the pad would only be limited by the manufacturing process. The present invention also relates to methods of making the flexible and wound sealing hemostatic pad.

BRIEF DESCRIPTION OF THE DRAWINGS

A full and enabling disclosure of the present invention, including the best mode thereof directed to one of ordinary skill in the art, is set forth in the specification, which refers to the appended drawings, in which.

DETAILED DESCRIPTION OF PREFERRED EMBODIMENTS

Figure 1:
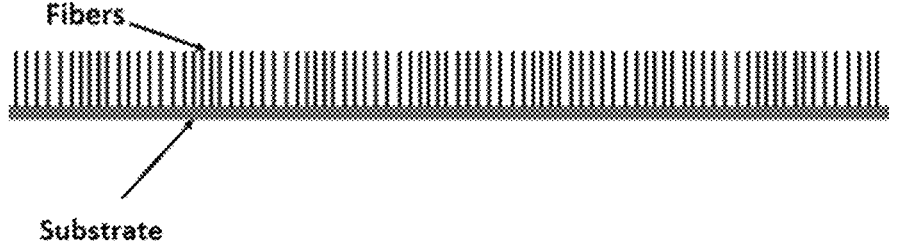
FIG. 1 illustrates the fibrous backing with fibers extending from the substrate where a portion of the fibers extend vertically from the substrate.

Reference now will be made in detail to the embodiments of the invention, one or more examples of which are set forth below. Each example is provided by way of explanation of the invention, not a limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. The following embodiments and aspects thereof are described and illustrated in conjunction with systems, tools and methods which are meant to be exemplary and illustrative and not limiting in scope. In various embodiments one or more of the above-described problems have been reduced or eliminated while other embodiments are directed to other improvements.

Thus, it is intended that the present invention covers such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

The pad is created by compression of a hemostatic powder to incorporate it into a fibrous backing having vertically oriented velvet-like fibers. Velvet is typically known as a type of woven tufted fabric in which the cut threads are evenly distributed, with a short dense pile, giving it a distinctive soft feel. For example, velvet materials are often made from a closely woven fabric of silk, cotton, or nylon, that has a thick short pile on one side. As used herein, the term "velvet-like" is defined as any fabric material that is velvet or that emulates the characteristics of velvet, is flexible, and has, at least on one side, a dense pile of fibers with at least some of the fibers extending vertically from the material.

The resulting pad formed from the hemostatic powder compressed into a velvet-like material substrate is flexible and is convenient to apply to any wound surface, including curved surfaces, compared to an inflexible tablet that is made without using a velvet-like material. The resulting pad, having better mechanical integrity than a tablet, can be made much larger, with much greater surface area, while using less hemostatic powder than a typical tablet. The resulting pad may also be cut into shapes if desired.

The inventive flexible hemostatic pad of this disclosure is prepared by pressure compaction of a hemostatic powder onto a velvet-like backing having at least partially vertical fibers extending upwardly therefrom. The inventive flexible hemostatic pad provides improved manufacturability and improved delivery and control of the application onto wound sites that are not substantially flat or that are larger than wound sites to which the known rigid compressed powder hemostatic tablets are typically used. The dense packing of a hemostatic powder into a flexible hemostatic pad form for a topical application adheres more tenaciously to certain wound sites than either the known hemostatic powders or the known rigid forms of the compressed tablets. In the rigid forms of the hemostatic tablets heretofore known, unused compressed powder will delaminate from the tablet/blood interface after time allows for fluid absorption expansion at the interface. Unlike the rigid tablets, the compressed powder from this inventive flexible hemostatic pad can either be designed to delaminate from the seal (like the rigid tablet), or be designed to separate from the velvet-like material just after application, leaving behind a power/blood seal, or the pad may be left in place to provide a reservoir of hemostatic dressing as a control for post application bleeding. These different designs are based on the amount of compressed powder and the length of the fibers in the velvet-like material, and is not possible without this combination of materials.

In discussing the fibers and hemostatic powder added to it, the words "onto" and "into" are used interchangeably herein. When used in such context, "unto" and "into" interchangeably mean that powder is incorporated into the fibers prior to or during compression. Then the compression binds the powder into the fibers.

The hemostatic powder may be a single uniform powder compressed into a tablet, or powders may be layered on top of the initial powder-compressed layer. These layers may be fully or partially compressed before adding additional powder, or layered as powder with a final compression or a combination.

To form the flexible tablet, the powder(s) and/or powder layer(s) are compressed onto a fibrous backing having at least some fibers that extend from and are at least partially oriented in a vertical direction relative to the backing. The compression can be performed to form the tablet by any known compression method into any size, shape, thickness and configuration. In addition, during product usage, various medical hemostatic compression assisting devices, such as balloons, compressed foams, mechanical clamps, and compression bandages can be used during the application of the hemostatic pad to a wound.

Such flexible hemostatic pads may be used as a topical dressing for bleeding control associated with minor wounds, including control of minor external bleeding and exudates from sutures and/or surgical procedures. The flexible hemostatic pad can either be applied to a wound that is actively bleeding or to a site that may experience bleeding later. The flexible hemostatic pad may be used to also seal a site that is oozing exudative bodily fluids and create a seal in combination with blood or exudative fluids to prevent maceration, while simultaneously preventing wound desiccation due to the seal that is formed.

The flexible hemostatic pad may be attached to adhesive bandages, swabs, surgical or dental instruments, vacuum devices, compression device, securement devices, or magnets, if the proper materials such as magnetite are mixed with the powder. The tools attached to the flexible hemostatic pad may be straight or bent, rigid or flexible. The securement devices may be a circumferential wrap for a body part with a way to prevent the wrap from dislodging. The wrap may apply pressure to the wound or simple hold the device in place. Compression devices may be used to apply pressure to a bleeding wound and such compression may be mechanical, pneumatic, hydraulic, or magnetic. Examples include, but are not limited to, preventing dislodgement by using adhesive to skin or adhesive bandages/ devices, Velcro® attachments, buttons, magnets, zippers, stitches, staples, or hooks. Securement means can be part of the pad, the pad may be attached to the securement device prior to application, or additional securement may be added after the flexible compressed hemostatic pad has been placed on the wound.

The hemostatic material (i.e., powder) should have certain characteristics. It should be sufficiently small so as to allow it to be incorporated into the fibrous backing. The hemostatic material must have a sufficient level of absorptive capacity to dehydrate the blood at the wound site to diminish and/or arrest bleeding. It should be sufficiently dry when processing into the flexible tablet so that it can be shaped and properly hold together as a pad or other solid form.

There are also certain characteristics of the flexible hemostatic pad that are beneficial. For example, if the hemostatic material compressed onto the backing is taller than the fibers themselves, the tablet can be removed after a given time from the wound site without causing re-bleeding. The pad needs to be sufficiently thin to be flexible, but sufficiently supported to be cut with a die.

Broadly, the hemostatic powder composition used to form the flexible hemostatic pad of the present invention may include an effective amount of an insoluble cation exchange resin material, which may be combined with an effective amount of an anhydrous salt ferrate compound, other antimicrobial agents or wound healing material. The resin may also be used alone. In one embodiment, the powder is pressed into the flexible hemostatic pad by incorporating the hemostatic powder with the backing having the velvet-like material.

The hemostatic powder portion of the flexible hemostatic pad may include a mixture of the hydrogen form of a cation exchange resin (henceforth notated in short as "hydrogen resin") and an anhydrous salt ferrate compound such as potassium ferrate.

Optionally, other materials can be incorporated into the hemostatic powder to enhance performance or add useful features, such as: antimicrobial agents; zinc oxide, Vitamin C, collagen; processing aids or performance enhancers such as binders, lubricants, and excipients including, but not limited to materials such as magnesium stearate; absorbing components, such as absorbent polymers, such as super-absorbent polymers; natural and/or synthetic gums, including but not limited to sodium carboxymethylcellulose and/or hydroxymethyl cellulose; nutrients, such as vitamin C; colorants, such as titanium dioxide; polyvinylpyrrolidone; and/or fibers (in addition to the fibers extending from the backing material) such as medical grade fibers may be for added strength, natural and synthetic gums. The materials can be added to the hemostatic powder during formation or may be added to the flexible hemostatic pad after formation. Similarly, materials may be incorporated into any portion of the backing material to provide wound benefit, such as, but not limited to, silver, chlorohexidine, and polyvinylpyrrolidone.

It may be necessary for the primary packaging of the pad to have moisture barrier properties; in which case the packaging will need to be compatible with energy forms of sterilization. The packaging may also be designed in such a way to protect the product from damage.

The powder component of the flexible hemostatic pad of the present invention can be made as follows.

Ion exchange resins are typically prepared as spheres with a particle size that typically range from less than 10 microns for high pressure liquid chromatography, from 40 to 250 microns for ingestible drug delivery resins, and from 300 to 1200 microns for some industrial applications. These sizes are fully hydrated sizes, because the vast majority of all ion exchange resin is used in the fully hydrated state. Resin, as manufactured, has an average size (diameter) with a Gaussian distribution, and the variation of bead size is based on the manufacturing process. The resin can then be further sized by grinding and/or fractional screening to acquire the proper size to suit an application. For drug delivery systems, similar sizes with a narrow Gaussian distribution are needed to ensure consistent delivery. For industrial liquid processing applications using an ion exchange resin bed, if the size distribution is too broad, the bead stacking will be affected and flow characteristics through the bed will be impeded, resulting in high pressure drops across the column of the ion exchange resin. The pressure drop increase occurs because the smaller particles can fit into the spaces between the larger particles, thus impeding liquid flow. Ion exchange resin crosslinking affects moisture absorption.

When a dried strong acid cation resin, such as one in hydrogen form ("SACR-H"), is applied to blood, the SACR-H floats on the blood surface, rapidly absorbing liquid from the blood. The pores of the resin are too small to absorb blood solids or large proteins. This rapid absorption of the liquid, while excluding the blood solids, causes the solids to stack up beneath the SACR-H. These solids continue to stack until the liquid can no longer be transferred through the barrier of blood cells that have been formed. If this barrier is pushed into contact with a surface it will adhere to the surface, due to the natural glue-like nature of dried blood. If this surface is a bleeding wound, then the barrier will adhere to the wound site and stop further bleeding.

If a dried, essentially round, SACR-H beads are poured onto a bleeding site, the beads that contact the blood will adhere to the blood, but additional beads will simply roll off the wound site, particularly if the wound site is not positioned horizontally, but is instead more vertical such as the neck, chest, or head region of a standing patient. This is also observed where the wound site is on a curved portion of the body, such as an arm, finger, or toe. A monolayer of beads that may adhere to such rounded or more vertically positioned skin surfaces will provide less adequate absorption capacity and a reduced ability to stop a bleeding wound without multiple applications. Several layers may be needed to absorb sufficient liquid from the blood to create a barrier of sufficient strength to stop bleeding from a wound. Flowing blood, continually eroding away the powder, may remove any hemostatic benefits of the powder.

In order to solve this need to adhere more of the powder at the wound site, the resin may be ground to smaller particles so that the angle of repose when the powder is applied is increased because the frictional contact area from particle to particle (i.e., cohesion between particles) is increased. Typically, the amount of unground, relatively round beads remaining in the inventive powder will be 5% or less in the final powder.

This increase in angle of repose allows for multiple layers of powder to re-main over a bleeding wound while reducing the amount of material that readily falls off the wound site during application. In addition to an increase in angle of repose, the increased angularity also allows the product to adhere better to a more inclined or curved wound surfaces.

SACR-H has a negative pKa (indicative of a strong acid), similar to that of hydrochloric acid. When applied to blood, a portion of the hydrogen atoms attached to the resin backbone are neutralized, but the remaining hydrogen atoms on the resin backbone have anti-bacterial properties. Due to stacking properties, if whole beads are applied and adhered to a blood barrier above a wound, there will be spaces between the beads large enough for bacterial intrusion versus the tightly spaced packing created by a more finely ground SACR-H product.

To increase the adhesion of the powder to all skin surfaces by increasing the cohesion amongst the particles, appropriate starting materials with the appropriate grinding and screening methodologies are employed. Screening out the "too low" and "too high" fractions or particle sizes results in a narrower and lower range of particle size distribution allowed by the present invention in order to provide the required adhesiveness to the wound.

SACR-H used in the hemostatic powder may be purchased from a supplier as spherical beads ranging in size from 150 to 1000 microns after drying to a moisture content of less than about 3% (although, typical drying results in a moisture content of approximately 1% or less). The dried SACR-H resin beads are then ground to a suitable particle size distribution to disperse onto a wound to result in a good adhesion to reduce the amount of powder that fails to adhere to the wound and simply falls off the skin surface during application.

The hydrogen resin may be the hydrogen form of 2% crosslinked, sulfonated polystyrene resin. The hydrogen resin may be available in whole insoluble, generally round, beads having an average particle size of approximately 500 microns in diameter (for purposes of this specification, "diameter" and "particle size", with respect to a particle or particles, are synonymous), or alternatively, the resin may be available in, or ground into, much finer fragments averaging in size from 80 microns to 200 microns in diameter.

One resin that may be employed in making the present invention is the hydrogen resin Purolite® CT122 available from Purolite Corporation of Bala Cynwyd, Pennsylvania. However, it will be understood by one of ordinary skill in the art that other hydrophilic cationic resins may be used. For example, other forms of resins may also be used, including but not limited to sodium resin and calcium resin. While such resins would work, the disadvantage of their use is that the more acceptable pH effect found in the hydrogen resin form may be diminished. In addition, resins having up to 10% or more cross-links may also be useful in the present invention.

The resin employed may have various particle size distributions, including but not limited to, 1) up to 10% of greater than 1400 microns; 2) up to 5% of less than 850 microns; or 3) up to 2% of less than 425 microns, with the primary particle size range being from 850 microns to 1400 microns.

A ferrate may be added during the powder preparation. The ferrate may be purchased or may be produced by cooking iron oxide with an oxidizing agent and then heating, until ferrate "cakes" are produced. When ferrate cakes are used, the cake is broken into smaller pieces, typically manually or with known machinery, and then a knife grinder, or other known suitable device, is used to break up the cake. In a typical instance, a knife grinder with a 2 mm screen may be used. This breaking process results in the ferrate having a particle size of 2 mm or less in diameter.

One particular ferrate that has proven useful when combined with the cationic exchange resin is potassium ferrate, which is the oxyacid salt byproduct of the reaction between ferric acid ($H_2FeO_4$) and potassium hydroxide (KOH). Potassium ferrate is manufactured by the thermal combination of iron oxide ($Fe_2O_3$) and potassium nitrate (KNOB). Potassium ferrate readily decomposes in water to produce $Fe_2O_3$ and KOH as follows:

$$2K_2FeO_4 + 2H_2O \rightarrow Fe_2O_3 + 4KOH + 1.5O_{2(g)}$$

The resin is initially dried, for example, in static dryer, such as an oven, at a temperature of approximately 100° C. to 110° C. for an average of 12½ days, depending on the ambient moisture. In one embodiment, the goal of drying the resin is to achieve a moisture content of 3% or less, and typically a moisture content of approximately 1%. During the drying process, the particle size of the resin is typically reduced due to the dehydration of the water molecules from the resin. Drying the resin reduces the ability for the resin to transport or exchange protons, and, therefore, a dry resin is rendered generally inert. It is necessary to dry the resin to a certain degree if the resin is to be mixed with another dry proton acceptor to deactivate the hydrogen transport mechanism but it is expected that moisture contents of as much as 25% may also be useful in the present invention.

Dried resin may be ground alone in an Attritor Mill at a production rate, for example, of 20 to 25 kg/hr. Unlike the Turbo Mill, an Attritor Mill is a stirred ball mill that uses larger hard stainless-steel spheres (for example, 9-10 mm in diameter) agitated by rotating agitator arms to crush smaller and softer material. The grinding action is caused by the impact of the stainless-steel spheres, agitator arms, and sides of the grinding tank. Particle size is controlled via agitator arm speed, size of grinding media, and grinding time. In one particular embodiment, the Attritor Mill is used to grind the dried hydrogen resin to an average particle size of approximately 40 microns (but one of ordinary skill in the art will appreciate that average particle sizes of up to 70 microns would be suitable for the present invention).

If ferrate is used, it is screened (typically 2 mm screen) and then, in certain embodiments, mixed with the dried resin at a ratio of 1:2 ferrate:hydrogen resin to obtain an approximately 1:7 weight mixture of ferrate:hydrogen resin, although weight mixtures ranging from 1:3 to 1:12 will adequately arrest bleeding, depending on the particular application. This mixture may then be subjected to grinding in a Turbo Mill (described above) using a 0.25 mm screen at a production rate, for example, of 20 to 25 kg/hr to obtain an intermediary product, which may either be processed immediately or stored in closed containers, such as plastic tubs, in order to deter rehydration until the powder can be processed into tablets.

It is to be understood that the described grinding and formation processes above could be utilized to form a wound sealing powder consisting of only the hydrogen resin (without the ferrate or pigment), and without the 3% moisture level constraint, as described in U.S. patent application Ser. No. 14/147,143, which is incorporated by reference herein in its entirety.

To form the flexible hemostatic pad, a substrate is employed to receive the powder and to be compressed with the powder. In particular, a backing may be chosen as the substrate and the backing may be fibrous. The backing may be natural fir material, woven or nonwoven material, or a flocked material, but all types of materials may prove useful in the present invention provided the fibrous backing has fibers extending away from the backing itself. The fibrous backing with fibers extending from the substrate where a portion of the fibers extend vertically from the substrate is illustrated in FIG. 1. The illustration of FIG. 1 is not a real-world example, but just for demonstration purposes.

Fibrous backings such as shown may be referred to as "velvet-like" because such backing have their fibers generally relatively evenly distributed over the backing surface as a short, dense pile. For use in the present invention, it is not required that the extending fibers be completely in the vertical direction or that they be evenly distributed. Fibrous backings may be used in the present invention if they have at least a sufficient number of fibers with at least partial vertical fiber portions extending in the vertical direction away from the backing. For purposes of this specification, "vertical" means extending away from the horizontal plane of the backing (if the backing is horizontal) in a generally straight line.

The use of such velvet-like materials as the backing allows for the use of a thin layer of hemostatic powder to be compressed into and onto the material, resulting in a tablet that is sufficiently flexible to be applied where more rigid hemostatic tablets cannot be applied because of the potential for cracking and breaking. In particular, a flocked, velvet-like material may be useful as the backing of the tablet.

The flexible hemostatic pad may be designed to be wetted from the backside of the device to facilitate removal from the wound to which the pad has been applied. This could be achieved in many ways, including but not limited to, including within the product certain types of porous materials.

In one embodiment, the invention may incorporate a thin layer of hemostatic powder, composed primarily of ion exchange resin (>80%) into a velvet-like material, then compressing those components into a final flexible pad. The pad may be used as a stand-alone device, may be incorporated into other devices such as, but not limited to, hemostatic compression devices, adhesive strips, cosmetically appealing substrates, rigid substrates, etc.

In one embodiment, the inventive flexible hemostatic pad formation provides an improved method of manufacture by eliminating the use of a female die as well as requiring significantly less compressing force to form the device compared to the hemostatic tablet without the velvet-like backing. The usual method to make a tablet requires the use of both a male and a female die. The female die is filled with powder and the fitted male die compresses the powder into a tablet, while the female constrains the powder into a limited space.

As part of this invention, the use of a velvet-like material removes the need for the female die, because the fibers prevent the powder from spreading laterally as the tablet is being compressed. In making the original inflexible tablet without the velvet-like material, the compression pressure required to produce a commercially stable and functional tablet is approximately 15,000 psi. The incorporation of the velvet-like material in making the flexible hemostatic pad significantly reduces the compression pressure from 15,000 psi to less than 7,500 psi (and in some cases to 7,244 psi). Although the exact amount of compression pressure will vary depending on various factors, including the particular type of material substrate, the amount of powder, and the type of powder used. The only constraint in choosing the compression pressure is to ensure that sufficient pressure is used to maintain the compressed powder on the substrate during application and allow the substrate to remain flexible.

The present 2-component flexible hemostatic pad allows for the creation of a pad that holds together, can be cut into shapes, and can be bent around a ½" PVC pipe to simulate its use on curved body parts such as the limbs. Less compression with the two components creates a lighter-colored finished pad than the darker inflexible tablet that uses a higher compression pressure.

The flexible hemostatic pad may be compression formed into different shapes or machined into different shapes after formation. Machining may be performed with blades, dies, compressed air or lasers and may be used to score larger pads to allow them to be broken into smaller shapes for application. The pad may be produced individually, in sheets, or be a continuous ribbon/roll of hemostasis pad material as any form of mechanical compression may be used. This allows for storage of the pad after compression for conversion into the final product at a later date.

In another embodiment, there is a powder depth at which the flexible hemostatic pad is no longer acceptable in terms of cracking and flaking properties. Cracking or flaking properties were tested in a laboratory using a compression die/anvil method and scissors. The pad was also bent around a ½" PVC pipe. Minor cracking is acceptable in the laboratory bend and cut test. Severe cracking and flaking are of more concern as the formed flexible hemostatic pad is bent or cut. Flaking is defined as when portions of the compressed powder flake away from the backing material after bending or cutting. During testing, the use of 0.7 mm and 2 mm powder heights produced acceptable 50 mm diameter flexible hemostatic pads. While the use of 4.3 mm-depth powder still formed a pad, a haloing effect was observed where the outside of the tablet appeared lighter than the inside due to differential compression forces as the powder on the outside of the pad was able to migrate as the die was pressed into the powder. The haloing effect of the 4.3 mm-depth powder pad may have been overcome by using much longer fibers to prevent powder migration during compression. In addition, the flexible pad made with the 4.3 mm-depth powder cracked and flaked as it was being bent and cut with a scissor. The 4.3 mm-depth powder product was still usable, and would be efficacious to stop bleeding, but may not be as cosmetically acceptable for some markets. Those of ordinary skill in the art can determine the maximum powder depth versus fiber length to avoid the degree of undesirability in cracking and flaking.

Figure 2:
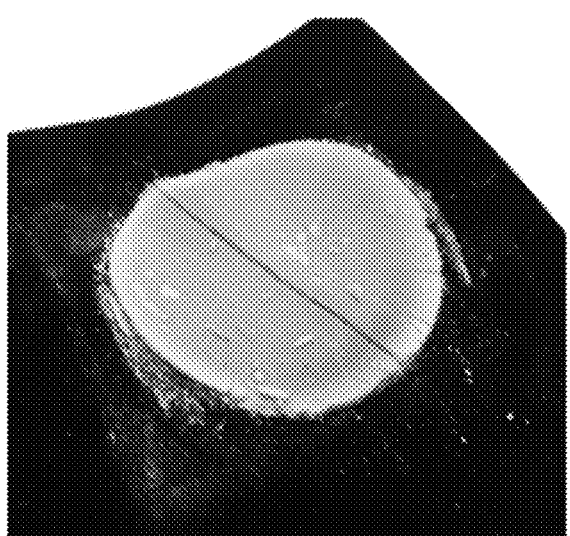
FIG. 2 is a photo of the 4.3 mm-depth product.

FIG. 2 is a photo of the 4.3 mm-depth product. The product is still viable and efficacious, but suffers some minor cosmetic imperfection after wrapping around a ½" PCV pipe, simulating a finger. This product would not experience cracking around a person's arm.

In another embodiment, the method of producing an optimum flexible hemostatic pad requires that the tendency to curl be controlled. The reason for curling is that the dry hemostatic compressed powder material absorbs moisture from the environment. This creates a difference of expansion between the top of the pad and the bottom. The compressed powder expands as it gains more moisture while the moisture resistant velvet-like backing maintains its shape resulting in curling or bending of the device toward the velvet backing due to longitudinal differences in expansion. One way of controlling the curling tendency is to increase the starting depth of the powder on the velvet-like material. For example, a pad made from 2 mm-depth powder curls significantly less than one made with 0.7 mm-depth powder. Other ways to control the curling tendency including starting with a less dry powder, making geometric cuts in the hemostatic pad, or adhering multiple smaller pads to a tertiary substrate.

In yet another embodiment to control curl in the flexible hemostatic pad, the pad may be flattened post-compression. If a powder contains less than about 20% moisture powder, the powder will absorb moisture from the surrounding atmosphere. The amount of absorption is based on moisture level of the starting powder, and the humidity of the air where the powder is stored. For example, assume a 20% moisture level is the equilibrium moisture (EM) of the powder. If a powder is compressed into a flexible hemostatic pad prior to reaching EM, or if the EM balance is changed, the resulting tablet will curl. This curling is a result of the powder being compressed in a fixed position and then expanding or contracting based on the change in moisture level to reach EM. A powder not at EM is compressed into a flexible hemostatic pad and then that pad is held flat and allowed to reach EM. The resulting flexible hemostatic pad at EM will not tend to curl or the curl will not be as drastic as a pad not held in position during the expansion.

This may lead to a manufacturing process where a pad is created and then placed in an environment to encourage EM acquisition. These pads may be precut or in sheets. This process may allow for rolls of intermediate product to be made, then cut into shapes (final shapes, or sheets for processing), to be "flattened" prior to packaging. If larger rolls of product are to be stored in manufacturing, direction and radius of the roll will be important to prevent the intermediate product from cracking.

In another embodiment, a pattern incorporating open space between flexible pads may be used to prevent curling of the flexible hemostatic pad. The pattern would allow the expanding compressed power space to expand, alleviating or reducing the propensity to curl. This pattern may be created by one of the examples, but not limited to, at the time of applying the powder to the velvet-like fabric, at compression using a patterned compression tool, after compression by creating a pattern in the surface of the compressed powder while leaving the velvet-like fabric backing intact, or by adhering individual strips or small tablets to a backing.

Another embodiment includes the creation of the velvet-like material from a more freely longitudinally expanding material. Such a material needs to be a four-way stretch material. Examples include, but are not limited to, elastic, spandex, rubber, latex, neoprene, nitrile, vinyl, or blend of material.

Another embodiment employs a sufficiently rigid velvet-like material to prevent curling or the adherence of the flexible pad to a more rigid substrate.

In another embodiment, the backing may be flocked into an irregular shape and the powder pressed directly onto that shape. That shape may be flexible or rigid but the solid layer itself will remain flexible. Examples of such shapes include a cup for a finger avulsion, a surgical glove, a hemostasis compression device, a hemostatic balloon, and other shapes. This may require compression tooling to better fit such shapes.

In another embodiment, two components may be used to make a stronger, thinner flexible hemostatic pad. A thinner pad may be advantageous in the medical industry to fit around vascular catheter lines to lay nearly flat against the body and prevent "kinking" of the line. This type of product may need a more rigid support to improve application and prevent curling of the flexible pad.

In another embodiment, the flexible hemostatic pad may employ simple slits, and/or holes through the pad to allow it to be manipulated around a vascular catheter or other lines or tubes in a patient. The flexibility of the pad allows the slits to create flaps that open and fit hemostatic-tightly around the line or tube. This is not possible using the prior rigid tablets that need to be designed with a complete through hole, in two halves.

In another embodiment, a much larger flexible hemostatic pad may be produced. Such products may have benefits in the military or EMS environment or as a floor cover for a blood spill until it could be properly cleaned.

In another embodiment, the flexible hemostatic pad can be designed to have localized tablet dislodgement shortly after application. In this embodiment, when the flexible pad is applied to a wound, only the portion of the compressed powder that contacts the blood will dislodge from the velvet-like material and form a seal over the wound. This removal can take place as soon as hemostasis is achieved. This ability of the pad is in contrast to a rigid StatSeal® tablet of compressed of powder. If removed too early, tablet delamination will remove the seal, resulting in a rebleed of the wound.

Figure 3:
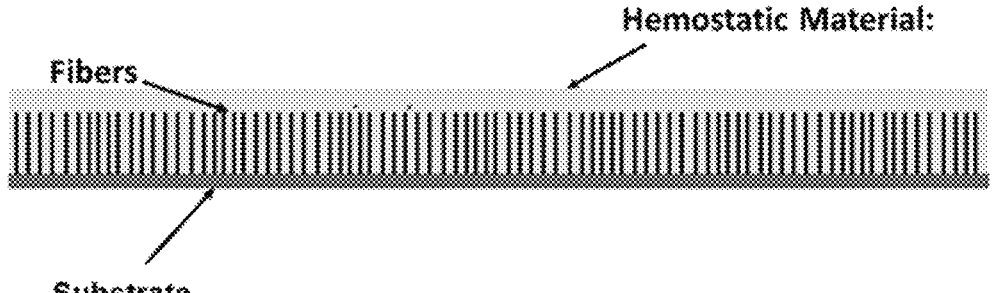
FIGS. 3 and 4 illustrate a hemostatic pad wherein the hemostatic powder is applied to the fibrous velvet-like substrate in a uniform layer, then compressed into the substrate with a compression force sufficient to create an integral shape.
Figure 4:
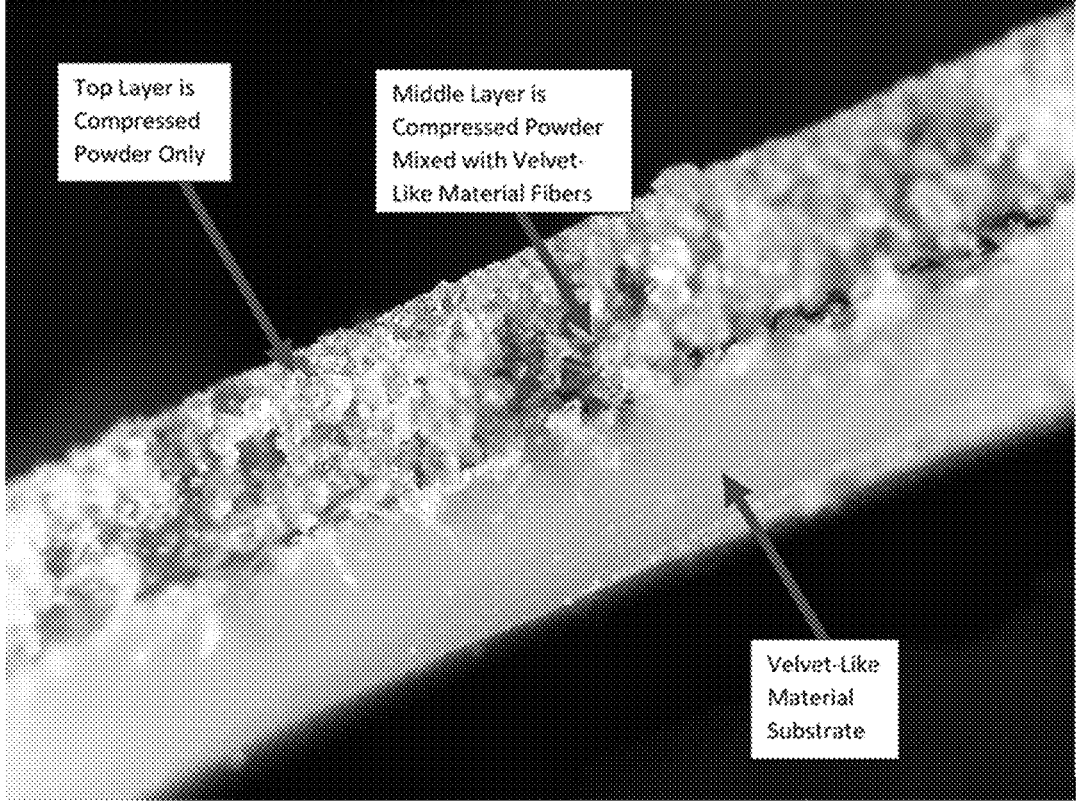

Typically, the hemostatic powder will be applied to the fibrous velvet-like substrate in a uniform layer, then compressed into the substrate with a compression force sufficient to create an integral shape for the hemostatic pad as shown in FIGS. 3 and 4.

Figure 5:
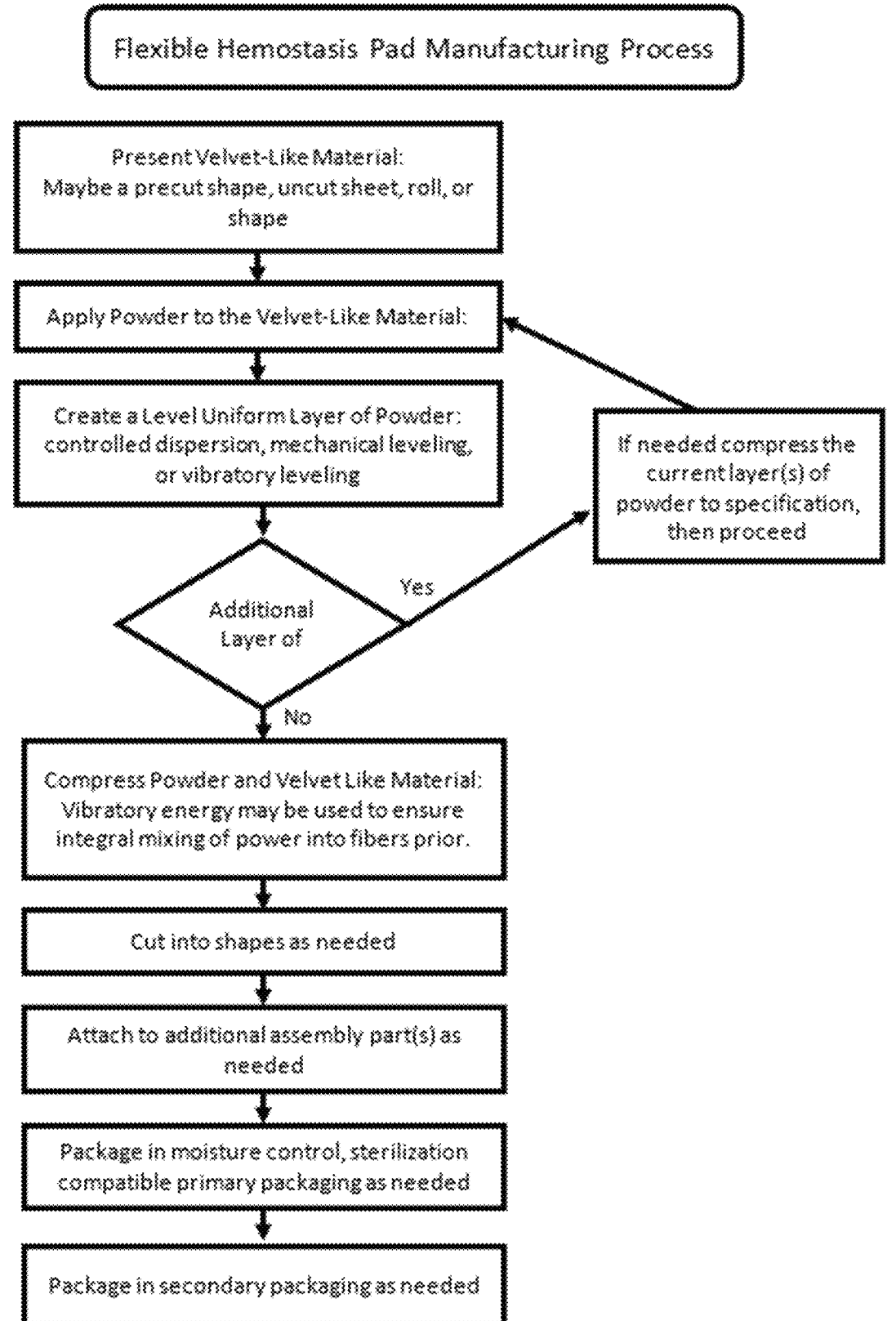
FIG. 5 is an exemplary flow chart for manufacturing the present invention.

The uniform layer may be created by direct-controlled dispersion, a leveling mechanism or vibratory leveling. There may be a single layer or multiple layers with no, partial or full compression during each step of the layering process. FIG. 5 is an example of a manufacturing flowchart.

In the process outlined above, the pre-height will be taller than the post-height to each component. The overall and relative height for the fibers and powder may change, depending on materials and desired removal effect, but the height of the fibers and hemostatic material will change as a result of compression. After compression, the fibers and hemostatic material will be locked together.

The powder or multiple layers of powder may be applied to the fibrous substrate in a uniform manner to allow for equal distribution of the compression force during the manufacturing process. A single, or multiple, application compression process may be used. In a multiple compression manufacturing process, the previous compression may be of the same or different compression force as subsequent compressions.

Various compression devices may be used, including but not limited to, mechanical and hydraulic presses or rolling presses that utilize compression rollers.

Orientation of materials during manufacturing may be with the backing on the bottom, then a powder layer, with compression from a die pushing downwards. Another method of manufacturing is to fill a cavity with powder to the appropriate depth, then apply the backing to above the cavity/powder, and compress the components together. Applying powder to the flexible, velvet-like material may prove difficult to create a uniform layer. Accordingly, the second method may be preferred because it may produce a more uniform layer of powder. This second method may also be more conducive to continuous manufacturing employing a roll of backing.

In the manufacturing process, there is often a need to control or regulate the temperature of the tooling. Temperature control may assist in pad formation or prevent sticking of either of the contacting materials with the tooling.

The fiber length should be engineered in light of the desired final product and its use. For example, a longer fiber length will typically be desired for a semi-flexible product and shorter fiber length desired for a more flexible product. Also, fiber length and adhesion strength of the glue holding the fibers to the backing may have a correlated impact on the force needed to remove the pad from a bleeding site, and how much of the compressed powder remains on the bleeding site.

Figure 6:
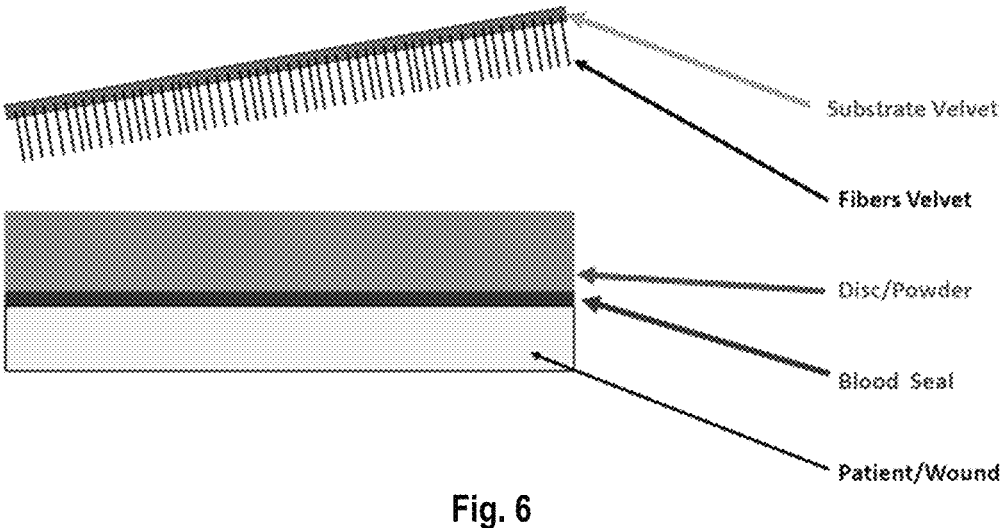
FIG. 6 illustrates the removal aspect when the compressed powder layer is left behind on the wound.
Figure 7:
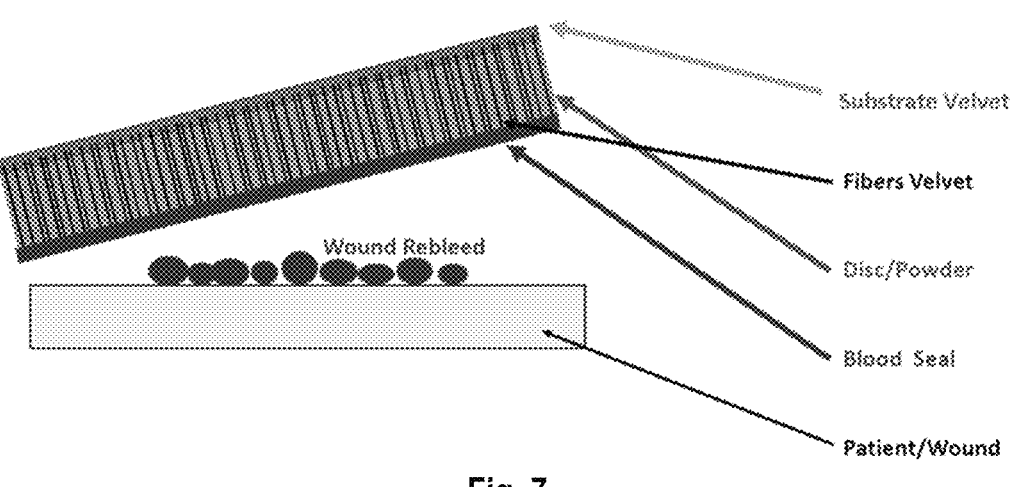
FIG. 7 illustrates the removal aspect when most of the compressed powder is removed when the pad is removed.

FIGS. 6 and 7 are meant to illustrate the removal aspect of differently designed pads based on the manipulation of the powder depth, fiber length, and fiber adhesion to the velvet-like substrate.

The product illustrated in FIG. 6 is designed to leave the compressed powder layer behind on the wound, being advantageous in normal Rx or OTC usage.

The product illustrated in FIG. 7 is designed to remove most of the compressed powder when the pad is removed, leaving behind less powder on the wound. This may result in a wound rebleed. This would be advantageous in a military, EMT, triage-type setting.

In another embodiment, the flexible hemostatic pad may employ a dual-sided velvet-like material compressed product instead of a single-sided product. This would make application in a limited light environment easier, because both sides of the product would be equally effective at hemostasis. A dual-sided product may help to limit the propensity of curling as well.

EXAMPLES

Initial testing utilized a thin layer of a ground, strong acid cation resin in hydrogen form, at 19% moisture, spread over a velvet-like material. Two pads were successfully created by compressing the hemostatic powder and fibrous backing to form the flexible hemostatic pad.

Additional testing revealed that pads formed using backings with various fiber lengths, and employing various powder heights were acceptable in terms of flexibility and strength as set forth below in Table 1. Note that "powder height" refers to pre compression powder height.

15

TABLE 1

| Velvet-like material | Powder height (mm) | Metric tons compression | Flexed Without crack-ing | 30 mm round due was used to produce |
|---|---|---|---|---|
| Long (1.5 mm) | 0.84 | 15 | Yes | — |
| Long (1.5 mm) | 0.84 | 10 | Yes | Flexed easily, but poorly formed tablet |
| Long (1.5 mm) | 0.84 | 12 | Yes | — |
| Long (1.5 mm) | 2.00 | 15 | Yes | — |
| Long (1.5 mm) | 2.87 | 15 | Yes | — |
| Long (1.5 mm) | 5.00 | 15 | No | This tablet cracked when wrapped around a finger but did not fall apart. It was very strong and didn't bend easily. |
| Short (1 mm) | 2.87 | 15 | Yes | The shorter fibers performed as well as the longer fibers. |
| Long (0.5 mm) | | 15 | No | This final tablet was 2.2 mm thick. It severely cracked when wrapped around finger but did not fall off velvet backing. |

The products were also tested for delamination of the hemostatic material. All products were easily removed with the addition of water. All pads left a layer of powder on the wound after removal.

Figure 8:
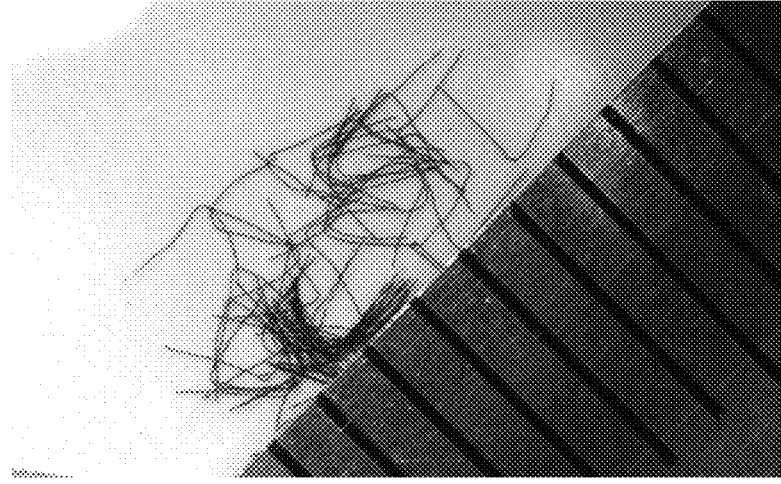
FIG. 8 shows longer fibers that are woven into the fabric material, without powder.
Figure 9:
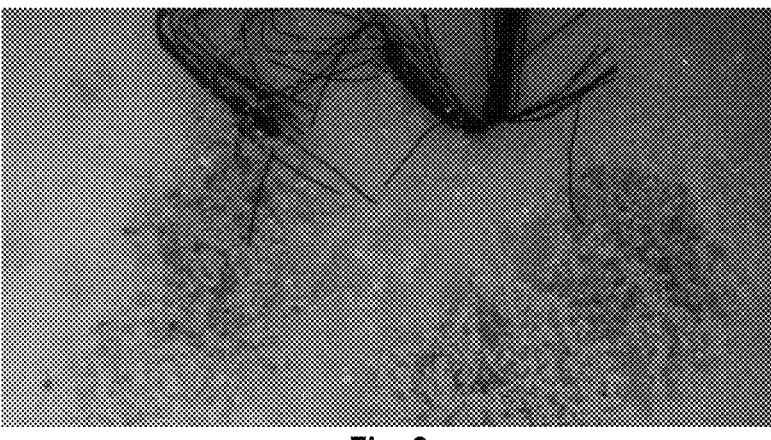
FIG. 9 shows longer fibers that are woven into the fabric material, with powder.

FIG. 8 is a photograph showing longer fibers with powder and FIG. 9 is a photograph showing longer fibers without powder. These fibers are woven into a fabric material.

Figures 10, 11:
FIG. 10 shows shorter fibers that are flocked/glued on the fabric material without powder.
FIG. 11 shows shorter fibers that are flocked/glued on the fabric material with powder.

FIG. 10 is a photograph showing shorter fibers with powder and FIG. 11 is a photograph showing shorter fibers without powder. These fibers are flocked/glued onto a fabric material.

Figure 12:
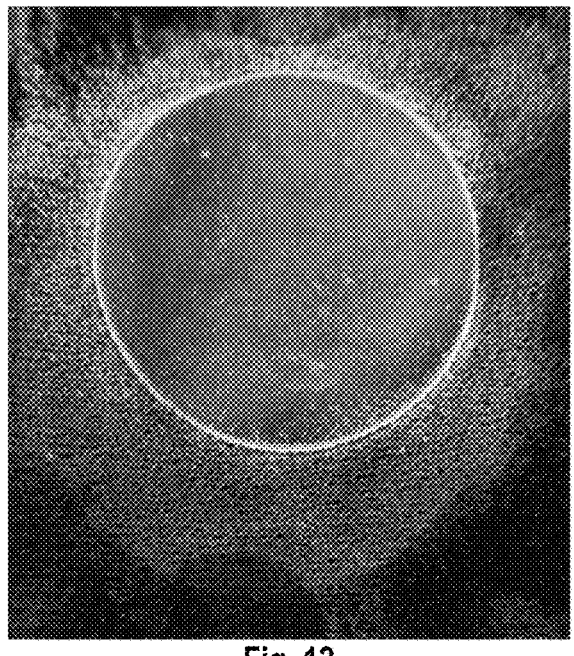
FIG. 12 is a photograph showing a flexible hemostatic pad formed onto/into a velvet-like backing.
Figures 13A, 13B, 13C, 13D:
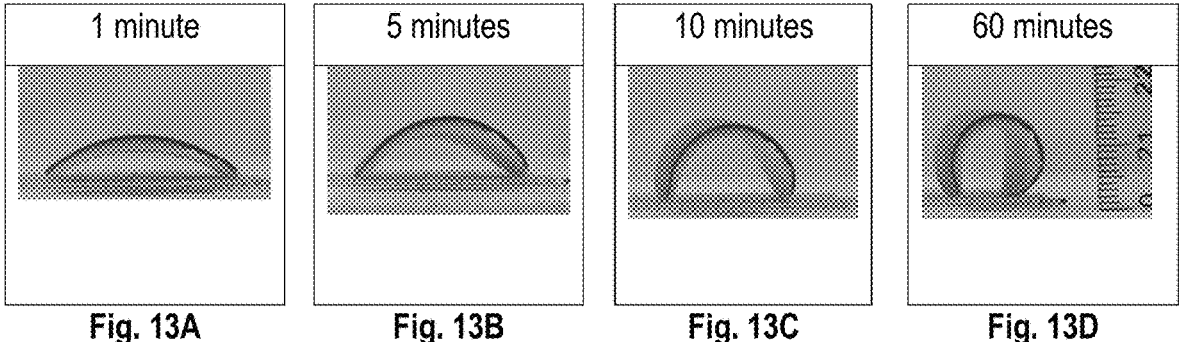
FIGS. 13A, 13B, 13C and 13D are photographs illustrating curling effects of the pad using dry powder, with the ruler measurements in millimeters.

FIG. 12 is a photograph showing a flexible hemostatic pad formed onto/into a velvet-like backing.

Below are the results of compressing the powder into the velvet-like material at different pounds per square inch (psi).

Compression Study

| | PSI | Cuts Good & ½" PVC pipe bend test with no major crack/flake |
|---|---|---|
| 50 mm Round Die | 1,811 | Fail |
| | 3,622 | Fail |
| | 7,244 | Pass |
| | 14,488 | Pass |
| 20 mm Round Die | 13,583 | Pass |
| | 22,638 | Pass |
| | 31,693 | Pass |
| | 45,275 | Pass |

FIGS. 13A, 13B, 13C and 13D are photographs illustrating the curling effects of the pad using dry powder. The ruler measurements are in millimeters.

Figure 14A:
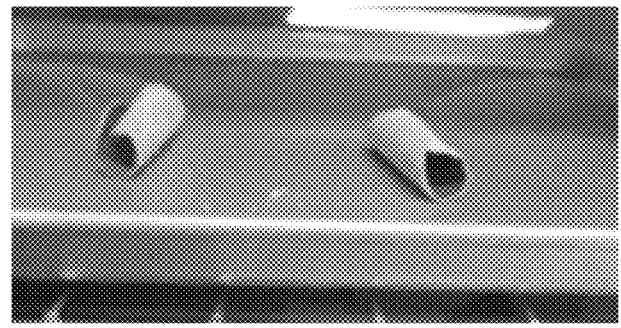
FIGS. 14A and 14B show examples of a curled pad heated in a small toaster oven to demonstrate the uncurling of the pad.
Figure 14B:

Heat can be used to drive moisture from the polymer to reverse the curling effect. FIGS. 14A and 14B are photographs showing examples of a curled pad heated in a small toaster oven to demonstrate the uncurling of the pad.

The flexible hemostatic pad exhibits very strong hemostatic properties in vitro testing, well above the mean arterial pressure (MAP) for a human of 70-100 mm Hg. Using various velvet backings in forming the flexible hemostatic pad, pressures of a range of at least 400 mm Hg to greater than 700 mm Hg were achieved, much higher than MAP. The hemostatic strength was tested on application of the pad to porcine blood. The pads were produced with powder depths of 0.7 mm to 2 mm.

An acrylic block with a ¼" horizontal hole drilled half-way through the block, intersected by a ⅛" vertical hole from the surface to the ¼" hole was the testing apparatus employed. EDTA-stabilized whole porcine blood was applied around the ⅛" surface hole. Then, the pad was applied and held in place for two minutes. After two minutes, a syringe containing air was used to pressurize the system through the horizontal ¼" inlet hole. Air pressure was recorded via data acquisition with the end point being when the seal failed or the max output of the pressure transducer was reached. During the air pressurization process, no mass was used to hold the pad in place. This test measured the burst strength of the blood/powder seal that had formed. Any additional mass above the pad would contribute to the hemostasis abilities of the pad.

Figure 15:
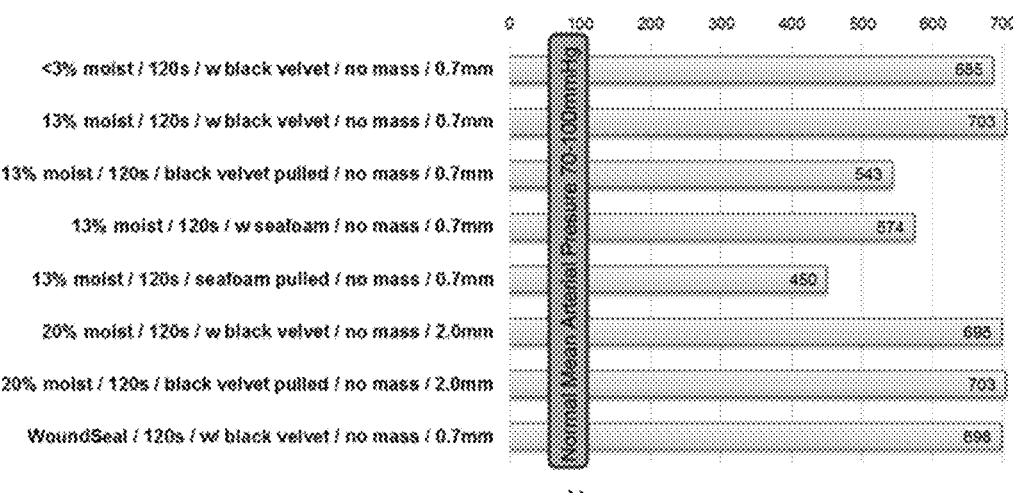
FIG. 15 is a graph of the test results from using different moisture level resin (up to 20%), with different velvet-like materials, and different powder heights prior to compression.

The results of that testing using different moisture level resin (up to 20%), with different velvet-like materials, and different powder heights prior to compression are shown in FIG. 15. All test samples held pressure significantly above MAP of 70-100 mmHg blood pressure.

Figure 16:
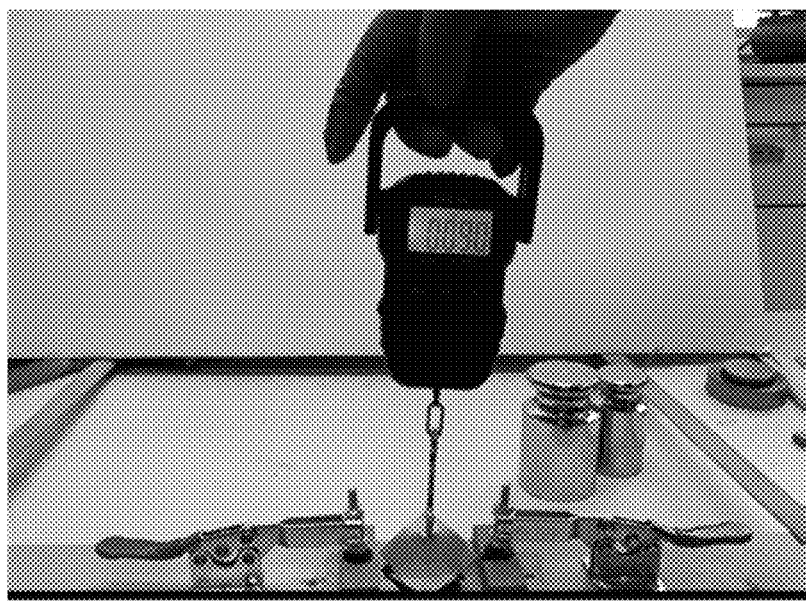
FIG. 16 is a photograph showing the pull force required to remove the pad from the simulated wound ranged from 0.1 kg to >1.1 kg.

In another example, the strength to remove the back from the powder/blood seal formed between porcine blood and the flexible hemostatic pad was measured. As illustrated in the photograph of FIG. 16, the pull force required to remove the pad from the simulated wound ranged from 0.1 kg to >1.1 kg. In general, pads made from the velvet-like backing with very short fibers were readily removed with 0.1 kg removal force and left the entirety of the compressed powder behind as the compressed powder separated from the velvet-like material. Pads made from velvet-like backings with long fibers required much greater pull force of >1.1 kg. The units in the chart below are kilograms.

| | Fiber Length (mm) | 5 min | 60 min | 24 hr | Average | Compared to Ama Velvet |
|---|---|---|---|---|---|---|
| 1 | 1 | 1.075 | 1.235 | | 1.155 | 100.0% |
| 2 | 0 3 | 0.100 | 0.065 | 0.175 | 0.113 | 9.8% |
| 3 | | Not tested - too similar to #5 | | | | |
| 4 | 1 | 0.640 | 0.700 | | 0.670 | 58.0% |
| 5 | 0.45 | | 0.665 | 0.680 | 0.673 | 58.2% |
| 6 | 0.48 | 0.515 | 0.455 | | 0.485 | 42.0% |
| 7 | 1.9 | >1.040 | Does not leave entire Disc behind at 5 mins | | | |

There is concern of fibers interacting with the wound during the healing process. If there is a complete layer of compressed powder above the fibers (no fibers exposed), then due to the near instantaneous seal-forming mechanism of action of the resin-based hemostatic product there will be no fibers contacting the wound. Therefore, there will be no interference with healing. Upon removal of the backing, there may be visible fibers, but these fibers will not extend through the depth of the powder to the wound. While not being of medical concern, any exposed fibers may present cosmetic issues and concern for the end user.

Figures 17, 18:
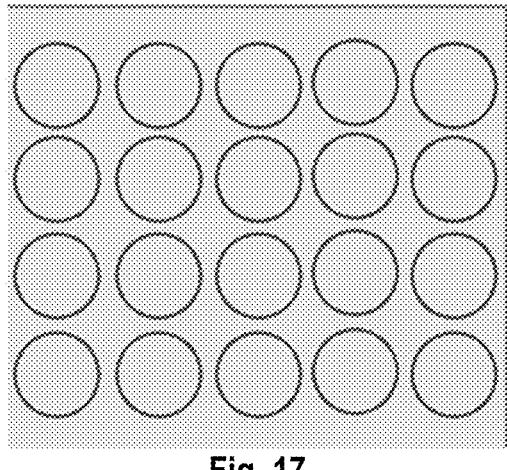
FIG. 17 illustrates a sheet of the pad product from which flexible pads can be cut.
FIG. 18 illustrates the pad shapes being fit around medical lines of tubes that are inserted into the human body.

In another embodiment, a sheet of the pad product could be created and then appropriately sized and shaped into final product flexible pads being cut from the sheet as shown in FIG. 17.

This could be done batch wise or on a continuous basis. For example, square-shaped adhered to a flexible adhesive strip to make a self-adhering flexible bandage to stop bleeding could be created. Examples of these cutting actions include, but are not limited to, scissor action, punch cut action, slicing action, tearing action, chopping action, high velocity impact action, laser cutting, and high-pressure air cutting.

In another embodiment, shapes could be cut designed to fit around medical lines of tubes that are inserted into the human body as shown in FIG. 18.

Figure 19:
FIG. 19 is a photograph of a 1.5" die cut round tablet.

Examples of these cutting actions include, but are not limited to, scissor action, punch cut action, slicing action, tearing action, chopping action, high velocity impact action, laser cutting, and high-pressure air cutting. FIG. 19 is a photo of a 1.5" die cut round tablet. The edges are clean with no visible fractures. This cutting action is not possible on a rigid compressed powder tablet.

Figure 20:
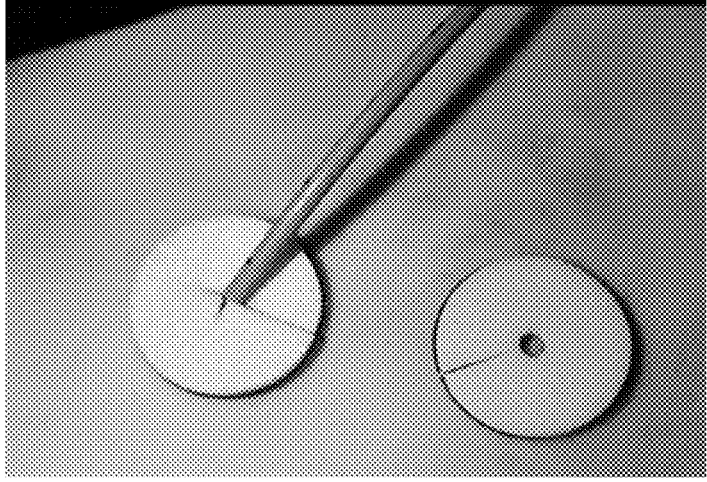
FIG. 20 is a photograph of die-cut design examples.

FIG. 20 is a photo of die-cut design examples.

Both are designed to fit around an indwelling vascular catheter. Notice how the flexibility of the pad allows for a good fit around the catheter. These are flexible pads adhered to a white foam cap.

Figure 21:
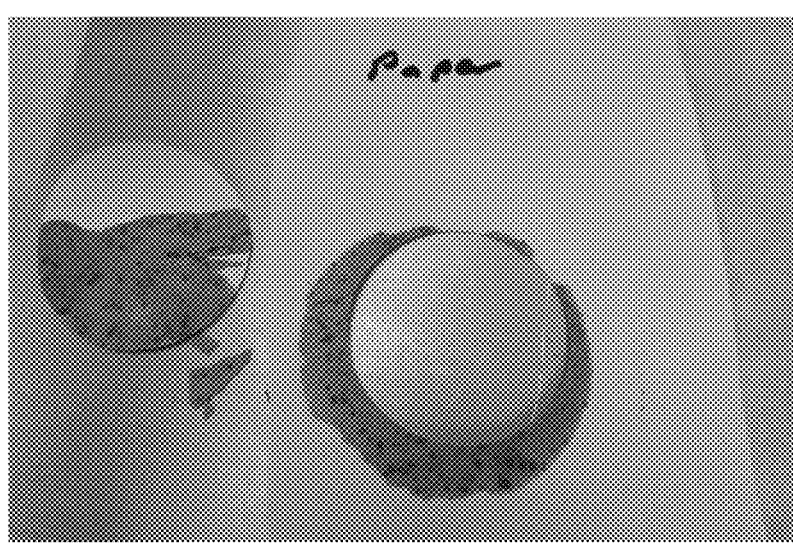
FIG. 21 is a photograph of the tablet after it was cut and wrapped around the ½" PVC pipe.

In another test, using similar conditions, (50 mm die with 20 k-kg compression), a tablet was created on a sheet of paper. The process of leveling the powder on the velvet-like material was easier than on the paper due to the increased friction of the velvet-like material with the powder that prevents powder from being dragged and leaving powder free areas on the backing. The resulting tablet (powder on paper) was more brittle and flaked off the paper readily. The flaking was apparent in both cutting the flexible pad configuration and wrapping it around a ½" PVC pipe. FIG. 21 is a photograph showing the tablet after it was cut and wrapped around the ½" PVC pipe. The edges of the tablet cracked and flaked off the paper backing.

Figure 22A:
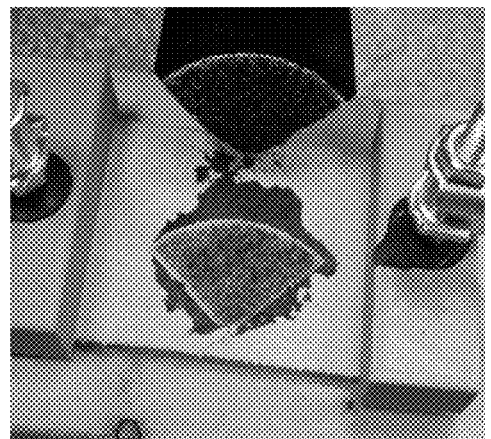
FIG. 22A is a photograph of a longer flexible product removed from a piece of velvet-like material.
Figure 22B:
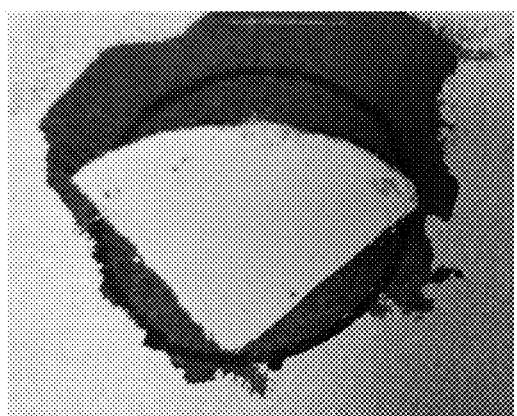
FIG. 22B is a photograph of a shorter flexible product removed from a piece of velvet-like material.

FIG. 22A is a photo of longer fiber flexible products, and FIG. 22B is a photo of a shorter-fiber flexible products both removed from a piece of velvet-like material.

In tests shown in FIGS. 22A and 22B, several droplets of whole bovine blood were applied to the unfinished side of a piece of leather. A flexible pad was placed atop the blood and held in place for two minutes and then removed. The test shown in FIG. 22A had a velvet-like material with longer fibers and more fibers remained on top of the compressed powder that was left behind. The test shown in FIG. 22B used a velvet-like material with shorter fibers, resulting in less fibers left behind.

The flexible hemostatic pad could be attached to a rigid or semi-rigid backing. An example of such a product is a flexible pad adhered to a stick-like device to produce an applicator to stop nosebleeds. Another example would be to attach the flexible pad to a stiff foam material to allow manipulation around vascular catheter lines, but still maintain a very thin shape. Another example is a hand-held plastic compression device to apply pressure to the groin for hemostasis post-arterial catheterization. Another example is a dental application post-tooth extraction.

In another example, 2% cross linked gel ion exchange resin left exposed to room conditions in ambient air conditions obtained a moisture of approximately 20% moisture. A flexible pad was created with dry resin, and this pad was placed on a piece of wood. A flat weight was placed on top and the pad. Three days later, the resulting pad was near equilibrium moisture with the room and did not curl when the weight was removed. The weight allowed the resin to expand as it absorbed moisture, but the hemostatic pad did not curl.

In another example, a droplet of blood was applied to a leather strip, the hemostatic compressed powder pad was applied and held in place. The area of compressed powder was much greater than the area of the blood droplet. It was expected that the entire flexible hemostatic pad would dislodge from the velvet-like material, but only the portion contacting the blood separated. This unexpected result of the flexible hemostatic pad will allow the pad to be adhered to a compression device and allow removal as desired post hemostasis without causing rebleed.

Compression devices that may be used to apply pressure to a wound include circumferential, mechanical, pneumatic, or hydraulic devices, a tourniquet-like device, or a standard military compression bandage. This will also make the flexible hemostatic pad applicable to an adhesive bandage for any wound.

Additional examples are directed to thicknesses of the pad in the range of 20-30 microns, including but not limited to, pads being 25 microns thick.

Other examples include the following:

A flexible hemostatic pad device, comprising a hemostatic powder compressed into a velvet-like backing with a minimum of 7,244 psi; a powder comprised primarily of hydrophilic polymer; a velvet-like material being a flexible surface with fibers extending vertically from the backing; a fiber length of less than 5 mm, a pre-compressed powder layer greater than the length of the fibers; a resulting compressed product less than or equal to 3 mm; said polymer is an ion exchange resin.

A semi-flexible hemostatic pad device, comprising a powder compressed into a velvet-like material with a minimum of 7,244 psi; a powder comprised primarily of hydrophilic polymer; a velvet-like material being a flexible surface with fibers extending vertically from the backing; a pre-compressed powder layer greater than the length of the fibers; a resulting compressed product greater than or equal to 3 mm; said polymer is an ion exchange resin.

A pad designed to remove most of the product when it is pulled from the patient for triage of bleeding patients or soldiers that comprises a powder compressed into a velvet-like material with a minimum of 7,244 psi; a powder comprised primarily of hydrophilic polymer; a velvet-like material being a flexible surface with fibers extending vertically from the backing; a velvet-like material where the attachment strength of the fibers is greater than the adhesive strength of the pad to the wound; a pre-compressed powder layer similar in height to the length of the fibers or shorter; a resulting compressed product less than 10 mm; a resulting compressed product that leaves <25% of the initial hydrophilic powder on the wound upon removal of the product from the wound, making wound clean up easier; said polymer is an ion exchange resin.

Hemostatic pads with irregular shapes or hard surfaces comprising a powder compressed into a substrate with a minimum of 7.244 psi; a powder comprised primarily of hydrophilic polymer; an irregularly shaped substrate consisting of a surface with fibers extending vertically; a pre-compressed powder layer similar or greater in height to the length of the fibers; a compression apparatus designed to match the irregular shape of the device to be converted to a hemostatic device; said polymer is an ion exchange resin.

Dual or multiple layer pad compressions comprising a powder compressed into a substrate; a powder comprised primarily of hydrophilic polymer; a substrate consisting of a surface with fibers extending vertically; an initial pre-compressed powder layer integrally mixed with the fibers; an additional layer of the same or different powder applied before or after an initial compression force to compress the fibers and powder together with fibers extending above the compressed powder; a final compression force of at least 7,244 psi to create a final product; said polymer is an ion exchange resin.

A die cut hemostatic pad comprising a sheet or roll of compressed powder into a velvet-like material cut into usable shapes; a powder compressed into a velvet-like material with a minimum of 7,244 psi; a powder comprised primarily of hydrophilic polymer; a velvet-like material being a flexible surface with fibers extending vertically from; a fiber length of less than 5 mm; a pre-compressed powder layer greater than the length of the fibers; said polymer is an ion exchange resin.

A cover attaching a flexible pad to a compression device or adhesive strip comprising a securement device, compression device, or adhesive device to designed to hold the hemostatic pad in contact with a bleeding wound; a powder compressed into a velvet-like material with a minimum of 7,244 psi to form a flexible hemostatic pad; a flexible hemostatic pad in a shape compatible with the securement device or compression device; a hemostatic pad attached to the securement device or compression device; a powder comprised primarily of hydrophilic polymer; a velvet-like material being a flexible surface with fibers extending vertically from the backing; a fiber length of less than 5 mm; a pre-compressed powder layer similar (within 3 mm) in height to the length of the fibers; said polymer is an ion exchange resin.

A cover attaching a flexible pad to rigid or semi rigid surface comprising a rigid or semi-rigid carrier; a powder compressed into a velvet-like material with a minimum of 7,244 psi to form a flexible hemostatic pad; a flexible hemostatic pad in a shape compatible with the rigid or semi-rigid carrier; a hemostatic pad attached to the rigid or semi-rigid carrier; a powder comprised primarily of hydrophilic polymer; a velvet-like material being a flexible surface with fibers extending vertically from the backing; a fiber length of less than 5 mm; a pre-compressed powder layer similar (within 3 mm) in height to the length of the fibers; said polymer is an ion exchange resin.

A packaged hemostatic pad package in moisture control packing to prevent curling comprising a hemostatic powder compressed into a velvet-like backing with a minimum of 7,244 psi; a powder comprised primarily of hydrophilic polymer; a velvet-like material being a flexible surface with fibers extending vertically from the backing; said flexible hemostatic pad packaging in a moisture barrier containing primary packaging to prevent curling; said polymer is an ion exchange resin.

A flexible hemostatic pad device comprising a hemostatic powder compressed into a velvet-like backing with a minimum of 7,244 psi; a powder comprised primarily of hydrophilic polymer; a velvet-like material being a flexible surface with fibers extending vertically from the backing; said velvet-like material constructed from a four way stretch material; a fiber length of less than 5 mm; a pre-compressed powder layer greater than the length of the fibers; a resulting compressed product less than or equal to 3 mm; said polymer is an ion exchange resin.

A double-sided flexible hemostatic pad comprising a powder compressed into a velvet-like material with a minimum of 7,244 psi to form a flexible hemostatic pad; a powder comprised primarily of hydrophilic polymer; a velvet-like material being a flexible surface with fibers extending vertically from the backing; a fiber length of less than 5 mm; a pre-compressed powder layer similar in height to the length of the fibers; a resulting compressed product less than 5 mm; said polymer is an ion exchange resin; said double flexible hemostatic pad is created by either adhering two single-sided pads together, folding over a single pad onto itself, or employing a dual sided velvet-like fiber holding compressed powder on each side of a relatively flat pad.

A flexible hemostatic pad held flat while reaching moisture equilibrium comprising a hemostatic powder compressed into a velvet-like backing with a minimum of 7,244 psi; a powder comprised primarily of hydrophilic polymer; a velvet-like material being a flexible surface with fibers extending vertically from the backing; a fiber length of less than 5 mm; a pre-compressed powder layer greater than the length of the fibers; a resulting compressed product less than or equal to 3 mm; said polymer is an ion exchange resin; said flexible hemostatic pad is held flat post final compression during manufacturing while being allowed to reach moisture equilibrium with the environment, resulting in a product with less propensity to curl when exposed to the atmosphere.

A flexible hemostatic pad with additional materials comprising a hemostatic powder compressed into a velvet-like backing with a minimum of 7,244 psi; a powder comprised primarily of hydrophilic polymer; a powder containing additional components; a velvet-like material being a flexible surface with fibers extending vertically from the backing; a fiber length of less than 5 mm; a pre-compressed powder layer greater than the length of the fibers; a resulting compressed product less than or equal to 3 mm; said polymer is an ion exchange resin; said additional component may consist of but not limited to solid flocculants to agglomerate blood solids, solid antimicrobial agents, solid antibacterial agents, liquid antimicrobial or antibacterial agents absorbed into said polymer, manufacturing processing aid, colorant, or a combination of such materials.

All references cited in this specification, including without limitation, all papers, publications, patents, patent applications, provisional patent applications, presentations, texts, reports, manuscripts, brochures, books, internet postings, journal articles, and/or periodicals are hereby incorporated by reference into this specification in their entireties, including all figures and tables, to the extent they are not inconsistent with the explicit teachings of this specification. The discussion of the references herein is intended merely to summarize the assertions made by their authors and no admission is made that any reference constitutes prior art. Applicants reserve the right to challenge the accuracy and pertinence of the cited references.

What is claimed is:

1. A flexible hemostatic pad comprising:
   a substrate comprising a flexible velvet-like fabric, wherein the flexible velvet-like fabric comprises fibers extending vertically from the substrate; and
   a hemostatic powder comprising an insoluble cation exchange material, wherein the hemostatic powder has been compressed into the velvet-like fabric to achieve a hemostatic powder depth of from 0.7 mm to no more than 2 mm, wherein the compressed hemostatic powder and the fibers are locked together, wherein the flexible hemostatic pad comprises a layer of compressed hemostatic powder disposed above the fibers, and wherein the compressed hemostatic pad into which the hemostatic powder has been compressed remains flexible and will not break when bent.

2. A flexible hemostatic pad comprising a velvet-like substrate comprising a flexible velvet-like fabric comprising fibers extending vertically from the substrate, and a hemostatic powder comprising an insoluble cation exchange material made by compressing the hemostatic powder into the velvet-like substrate with a compression force of between 7,244 psi and 10,000 psi such that the hemostatic powder has a depth of no more than 2 mm, wherein the compressed hemostatic powder and the fibers are locked together, wherein the flexible hemostatic pad comprises a layer of compressed hemostatic powder disposed above the fibers, and wherein the compressed hemostatic pad into which the hemostatic powder has been compressed remains flexible and will not break when bent.

3. The flexible hemostatic pad of claim 2 wherein the compression force is between 7,500 psi and 10,000 psi.

4. The flexible hemostatic pad of claim 2 wherein the compression force is approximately 7,500 psi.

5. The flexible hemostatic pad of claim 2 wherein the compression force is approximately 7,244 psi.

6. The flexible hemostatic pad of claim 2 wherein the compression force is between 7,244 psi and 8,000 psi.

7. The flexible hemostatic pad of claim 2 wherein the hemostatic powder is compressed into the velvet-like substrate to achieve a hemostatic powder depth of from 0.7 mm to 2 mm.

8. The flexible hemostatic pad of claim 1 wherein the hemostatic powder further comprises a salt ferrate.

9. The flexible hemostatic pad of claim 8 wherein the salt ferrate is potassium ferrate.

10. The flexible hemostatic pad of claim 1 wherein the hemostatic powder is compressed into the velvet-like substrate to achieve a hemostatic powder depth of 0.7 mm.

11. The flexible hemostatic pad of claim 2 wherein the hemostatic powder further comprises a salt ferrate.

12. The flexible hemostatic pad of claim 11 wherein the salt ferrate is potassium ferrate.

13. The flexible hemostatic pad of claim 2 wherein the compression force is between 7,500 psi and 8,000 psi.

14. The flexible hemostatic pad of claim 1 wherein the hemostatic powder is compressed into the velvet-like substrate to achieve a hemostatic powder depth of 2 mm.

* * * * *